United States Patent [19]
Sudo et al.

[11] Patent Number: 5,093,081
[45] Date of Patent: Mar. 3, 1992

[54] DRY-TYPE ANALYTICAL ELEMENT FOR IMMUNOASSAY

[75] Inventors: Yukio Sudo, Saitama; Yoshihiro Ashihara, Tokyo; Toshikage Hiraoka, Saitama; Isao Nishizono, Tokyo; Shigeki Kageyama, Saitama; Tetsuji Tanimoto, Tokyo, all of Japan

[73] Assignees: Fuji Photo Film Co., Ltd., Kanagawa, Japan; Fujirebio Kabushiki Kaisha, Tokyo, Japan

[21] Appl. No.: 369,332

[22] Filed: Jun. 21, 1989

[30] Foreign Application Priority Data

Jun. 24, 1988 [JP] Japan ............................... 63-155029
Jun. 24, 1988 [JP] Japan ............................... 63-155030

[51] Int. Cl.$^5$ .................................................. G01N 21/78
[52] U.S. Cl. ........................................ 422/56; 422/55; 422/57; 435/7.1
[58] Field of Search ............... 422/56, 57, 55; 435/7, 435/7.1

[56] References Cited

U.S. PATENT DOCUMENTS

| | | |
|---|---|---|
| 3,992,158 | 11/1976 | Przbylowicz et al. |
| 4,321,364 | 3/1982 | McCleary . |
| 4,363,874 | 12/1982 | Greenquist ............................ 422/56 |
| 4,390,343 | 6/1983 | Walter .................................... 422/56 |
| 4,472,498 | 9/1984 | Masuda et al. ......................... 422/56 |
| 4,757,001 | 7/1988 | Ashihara et al. . |

FOREIGN PATENT DOCUMENTS

| | | |
|---|---|---|
| 0040728 | 5/1981 | European Pat. Off. . |
| 0152305 | 2/1985 | European Pat. Off. . |
| 0254117 | 6/1987 | European Pat. Off. . |
| 0313858 | 9/1988 | European Pat. Off. . |
| 0310940 | 4/1989 | European Pat. Off. . |
| 2377630 | 1/1978 | France . |
| 61-80049 | 4/1986 | Japan . |
| 2052057 | 8/1979 | United Kingdom . |
| 2085159 | 8/1980 | United Kingdom . |

OTHER PUBLICATIONS

Chem. Abstracts, Sudo, Yukio, Analysis element for enzyme determination in aqueous sample or EIA. abstract vol. 112, No. 1, Jan. 1, 1990, p. 404, No. 4038x, Columbus, Ohio.

*Primary Examiner*—Christine Nucker
*Assistant Examiner*—Jeffrey Stucker
*Attorney, Agent, or Firm*—McAulay Fisher Nissen Goldberg & Kiel

[57] ABSTRACT

A dry-type analytical element for immunoassay having at least one water-permeable layer for measuring a ligand in a sample according to enzyme immunoassay, which comprises, (A) a water-insoluble macromolecular substrate, and
(B) an antibody, reacting with the ligand in the sample, conjugated with an enzyme capable of acting on the above water-insoluble macromolecular substrate.

The above analytical substance further comprises, (C) a macromolecular substance which is a conjugate of the ligand or its derivative with a macromolecular compound in the above water-permeable layer of the above dry-type analytical element.

The invention can conduct a highly sensitive and simple enzyme immunoassay.

10 Claims, 1 Drawing Sheet

DRY-TYPE ANALYTICAL ELEMENT FOR IMMUNOASSAY

BACKGROUND OF THE INVENTION

1. Field of the Invention

This invention relates to an immunologically useful dry-type analytical element for enzyme immunoassay utilizing antigen-antibody reaction.

2. Description of the Prior Art

Various methods are known for determining biochemical substances contained in a body fluid or the like, and among them, enzyme immunoassay is known as a method capable of measuring them in a relatively high sensitivity. On the other hand, the method of using a dry-type analytical element has also been developed in view of simplicity and rapidity (U.S. Pat. No. 4,292,272, U.S. Pat. No. 3,992,158, DE 33 43 695A, etc.). It has been desired to develop the dry-type analytical element for immunoassay eliminating both disadvantages of dry-type analytical element method and enzyme immunoassay by combining them. Thereupon, the inventors tried to incorporate the enzyme immunoassay using a water-insoluble macromolecular substrate as the substrate for an enzyme-antibody conjugate as described in Japanese Patent KOKAI Nos. 80049/1986 and 80050/1986 into dry-type analytical element. They have now succeeded in obtaining a dry-type analytical element for immunoassay wherein a water-insoluble macromolecular material as the substrate and an enzyme-antibody conjugate are incorporated. As a result they found that the analytical element does not require any complicated operation such as centrifuging the substrate or preliminary reaction such as an antigen-antibody reaction and can analyze rapidly by a simple operation.

SUMMARY OF THE INVENTION

An object of the invention is to provide a dry-type analytical element for immunoassay capable of conducting an enzyme immunoassay in a high sensitivity by a simple operation.

The above object has been achieved by a dry-type analytical element for immunoassay having at least one water-permeable layer for measuring a ligand in a liquid sample according to enzyme immunoassay, which comprises, (A) a water-insoluble macromolecular substrate, and
(B) an antibody, reacting with the ligand in the sample, conjugated with an enzyme capable of acting on the above water-insoluble macromolecular substrate.

The above object has also been achieved by a dry-type analytical element further containing (C) a macromolecular substance which is a conjugate of the ligand or its derivative with a macromolecular compound in the above water-permeable layer of the above dry-type analytical element.

DETAILED DESCRIPTION OF THE INVENTION

Figure 1:
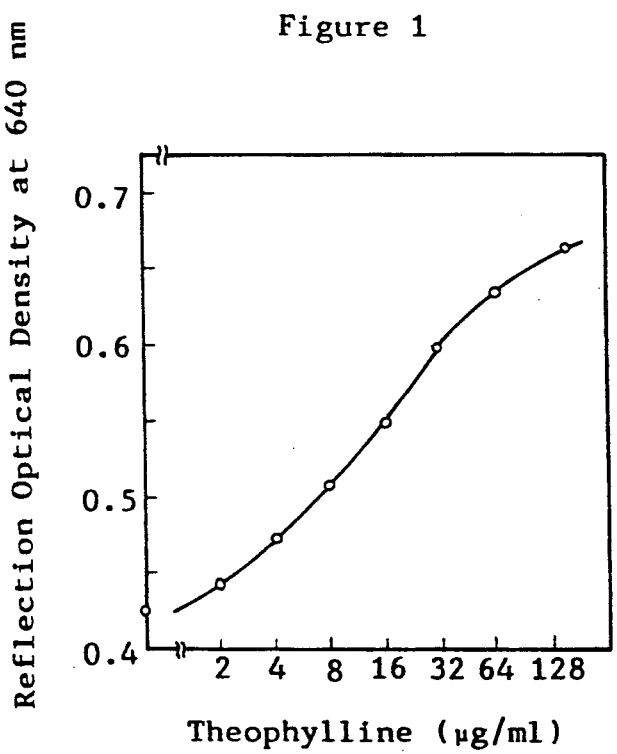
FIG. 1 indicates a calibration curve of theophylline using the dry-type analytical element for immunoassay obtained in Example 1.

Substances to be analyzed (analytes) of the dry-type analytical element for immunoassay of the present invention is a ligand having one or more antigenic determinants contained in a liquid sample. The kind of the sample is not definited, and includes humoral fluid such as whole blood, plasma, serum, lymph and urine. In the case of plasma, serum, lymph and urine, a special pretreatment is usually not necessary, and the sample may be measured directly.

The ligand has one or more antigenic determinants, and includes various antigens, existing in organs, blood or urine, such as medicinal substances including digoxin, theophylline, phenobarbital, phenytoin, penicillin and amikacin, or hormones, derived from various endocrine glands, including prostaglandin, testosterone, progesterone and thyroxin, or plasma proteins including immunoglobulin and albumin, or viral antigens including HB antigen, bacteria, or cancer-relating antigens such as α-fetoprotein, ferritin and CEA. The dry-type analytical element for immunoassay of the present invention is particularly effective for measuring a high molecular weight ligand, for example, having a molecular weight of more than 20,000. Furthermore, a low molecular weight ligand, for example, having a molecular weight of less than 20,000 can be measured by incorporating the macromolecular substance which is a conjugate of the ligand or its derivative and a macromolecular compound.

When the macromolecular substance is incorporated, the antibody conjugated with the enzyme reacts competitively with an antigenic determinant of the ligand to be measured and that of the ligand on the macromolecular substance.

The antibody specific to the ligand may be obtained according to a known method of producing an antibody. For example, the ligand or a protein binding of the ligand mixed with an adjuvant is injected once or several times into subcutaneous of dorsal skin, foot pad or femoral muscle of a warm-blooded animal, such as rabbit, goat, horse, guinea pig or chicken, in an amount of 0.3 to 2 mg per kg of weight, and thereby the antibody is produced in the humoral fluid. The serum may be used as the antibody, or it may be purified according to a known method for antibody, i.e. immunoglobulin, from serum.

On the other hand, this antibody may be obtained as a monoclonal antibody. In this case, the above ligand or the protein binding the ligand mized with an adjuvant is injected several times into the abdominal cavity of a mouse, and its spleen is excised. The spleen cell is fused with mouse myeloma cell by a conventional method such as by using polyethylene glycol. The hybridoma thus obtained is cultured and cloned, and the cell capable of producing the object antibody is selected. This cell is injected into the abdominal cavity of a mouse, and multiplied. Then, ascites are collected, and the object antibody is purified from the ascites. The antibody may be its fragment, such as F(ab')$_2$, Fab' or Fab.

Subsequently, the enzyme attached with the antibody acts on the water-soluble macromolecular substrate. It is convenient to use the enzyme of which activity can be easily measured. They include amylase, dextranase, cellulase, collagenase, mannase, protease, elastase, lipase and glucoamylase.

The water-soluble macromolecular substrate on which the enzyme acts includes substrates of the enzyme, such as starch, amylose, amylopectin, peptide and cellulose, and examples of other water-insoluble substrates are described in "Koso (Enzyme) Handbook" (Ed. Maruo et al, Asakura-Shoten, Tokyo, 1982) and "Seikagaku (Biochemical) Handbook" (Ed. The Japanese Biochemical Society, Maruzen, Tokyo, 1980).

A directly or indirectly detectable functional group or compound may be bound to the macromolecular substrate. The directly or indirectly detectable functional group or compound includes the compounds having a dye portion and the compounds capable of producing fluorescence or luminescence. It may be a dye-forming compound such as a coupler disclosed in U.S. Pat. No. 4,268,628, Japanese Patent KOKAI No. 59-30063 or the like. For the means to detect the above substrate having the directly or indirectly detectable functional group or compound, optical measurement of transmitted or reflected light at a maximum absorption wave length is suitable, while, visual observation may be employed according to the object or accuracy required. The optical measurement of fluorescence or luminescence is preferably carried out in the vicinity of main wave length of the fluorescence or liminescence. The binding method of the functional group or compound to the macromolecular substrate may be selected from the methods using a reactive dye disclosed in "The Chemistry of Synthetic Dyes" Vol. 6 (Ed. K. Venkataraman, Academic Press, 1972), the methods disclosed in U.S. Pat. No. 4,268,628, Japanese Patent KOKAI No. 59-30063 or the like. A preferred substrate having the directly or indirectly detectable functional group or compound dye-labeled starch which is starch chemically pound and dye.

The binding method of the enzyme and the antibody may be selected by considering the functional groups of both substances. Such functional groups include amino group, carboxyl group, hydroxyl group, thiol group, imidazolyl group, phenyl group, and the like. As to the binding method of amino groups, many methods are known such as the diisocyanate method, the glutaraldehyde method, the difluorobenzene method, the benzoquinone method, and the like. As the method of binding amino group to carboxyl group, the peptide-binding method of carboxyl group to succinimido ester, the carbodiimide method, the Woodward reagent method and the like are known. The periodate oxidation method (Nakane method) where a bridge between amino group and sugar chain forms is also utilized. In the case of utilizing thiol group, for example, a carboxyl group is first converted to a succinimido ester, and this ester group is then allowed to react with cysteine to induce the thiol group, and both thiol groups are bound by using a thiol-reactive bifuncional cross-linking reagent such as phenylenebismaleimide. As the method of utilizing a phenyl group, the diazotization method and the alkylation method are utilized. Other than the above, a suitable method may be selected from the various methods described in "Method in Immunology and Immunochemistry" (C. A. Williams et al., Academic Press, N.Y., 1976) and "Koso Meneki Sokutei-ho" (Enzyme Immunoassay)" (E. Ishikawa et al., Igaku-shoin, Japan, 1978). The molar ratio of the binding is not limited to 1:1, and suitable ratios can be selected. After the binding reaction, the antibody conjugated with enzyme is purified by gel filtration, ion-exchange chromatography or affinity chromatography or a combination thereof, and lyophilized, if necessary.

On the other hand, in the case that the sample contains an enzyme of the same kind as the enzyme of the conjugate, it is preferable that an enzyme inhibitor of which the degree to inhibit the enzyme in the sample is greater than the degree to inhibit the enzyme of the conjugate is allowed to be in contact with the enzyme in the sample.

The most desirable enzyme inhibitor inacivates the enzyme contained in the sample and does not inhibit the enzyme of the conjugate. However, it is practically sufficient that the blank value does not rise through the measurement, and the enzyme activity may be recovered after the measurement, such as by the inactivation of the enzyme inhibitor. The enzyme inhibitor may inactivate the free enzyme but not the enzyme bound to the antibody. The enzyme inhibitor may be a known enzyme inhibitor having such a specificity. Besides, when the enzyme contained in the sample is injected into a foreign warm blooded animal to produce the antibody to the enzyme, this antibody may also be utilized as the enzyme inhibitor. The production of the antibody may be carried out according to the method mentioned previously.

When the lowering of the enzyme activity by binding the ligand to the conjugate is insufficient in the case of measuring a high molecular weight ligand, it is preferable to use an another antibody, namely second antibody, specific to different antigenic determinant in the same ligand from that to the antibody conjugated with the enzyme. As the second antibody, for example, a mouse is immunized with an antigen to obtain monoclonal antibodies, and two or more kinds of the antibodies reacting with different antigenic determinants in the ligand are isolated. Then, one of the different antibodies may be used as the second antibody.

A ligand having a low molecular weight may be measured by adding the macromolecular substance being a conjugate of the ligand or its derivative with a macromolecular compound in the water-permeable layer of the dry-type analytical element for immunoassay of the invention, containing the water-insoluble macromolecular substrate and the antibody conjugated with the enzyme.

The ligand for preparation of the macromolecular antigen has one or more antigenic determinants common to the ligand in the sample, and it is usually the same substance as the ligand in the sample. The derivative of the ligand includes the compounds which has amino group, carboxyl group, thiol group or the like induced the ligand, and for example, 8-propylcarboxytheophylline is a derivative of theophylline.

Besides, the derivative of the ligand may be a derivative of a cross-reacting compound for the antibody against the ligand. For example, when the antibody specific to theophylline being the ligand cross-reacts with caffeine, a derivative of caffeine may be used as the derivative of theophylline.

In the macromoleular antigen, water-soluble macromolecular compounds having a molecular weight of more than 100,000 daltons are suitable as the macromolecular compound bound to the ligand or its derivative. The examples of such a macromolecular compound include polysaccharides and their derivatives such as soluble dextran, carboxymethyl dextran, dextran induced amino group and amylose, or proteins such as gelatin, hemocyanin and ferritin, or polyethylene glycol. They may be sufficient to satisfy the aforementioned conditions in a bound state to the ligand or its derivative, and include, for example, a polymer of a relatively lower molecule such as bovine serum albumin.

The macromolecular substance may also be a polymer of the ligand or its derivative. The polymerization method may be selected from the following binding methods of the ligand or its derivative to the macromolecular compound, and for example, the ligand or its derivative may be polymerized by using a bifunctional cross-linking reagent such as carbodiimide, glutaraldehyde or the like.

The binding method of the ligand or its derivative to the macromolecular compound may be selected by considering the functional groups of both substances. Such functional groups include amino group, carboxyl group, hydroxyl group, thiol group, imidazolyl group, phenyl group and the like, and the binding method of these groups may be selected from the aforementioned methods for binding the enzyme to the antibody. The molar ratio of the biding is not limited to 1:1, and suitable ratios can be selected. After the binding reaction, the conjugate produced is purified by gel filtration, ion-exchange chromatography, affinity chromatography or a combination thereof, and lyophilized, if necessary.

The dry-type analytical element of the invention may have similar layer constitutions to various known dry-type analytical element, such as a multilayer element containing not only the porous layer and the reagent layer described later but also a support, a spreading layer, a registration layer, a light-blocking layer or a light-reflecting layer, an adhesive layer, a filtering layer, a water-absorption layer, an under coat layer and the like. The examples of the analytical element having such a layer constitution are disclosed, for example, in U.S. Pat. No. 3,992,158 and U.S. Pat. No. 4,292,272.

In the case of using a light-transmissive water-impermeable support, the following layer constitutions are practically applicable to the dry-type analytical element for immunoassay of the invention. However, the layer constitutions are not limited to them.

(1) A spreading layer, a reagent layer and the support, superposed in this order.

(2) A spreading layer, a reagent layer, a registration layer and the support, superposed in this order.

(3) A spreading layer, a light-reflecting layer, a reagent layer and the support, superposed in this order.

(4) A spreading layer, a light-reflecting layer, a reagent layer, a registration layer and the support, superposed in this order.

(5) A spreading layer, a reagent layer, a light-reflecting layer, a registration layer and the support, superposed in this order.

(6) A spreading layer, a first reagent layer, a light-reflecting layer, a second reagent layer and the support, superposed in this order.

(7) A spreading layer, a first reagent layer, a light-reflecting layer, a second reagent layer, a registration layer and the support, superposed in this order.

(8) An immunoassay reagent-containing spreading layer, a registration layer and the support, superposed in this order.

(9) An immunoassay reagent-containing spreading layer, a light-reflecting layer, a registration layer and the support superposed in this order.

In the above layer constitutions (1) to (5), the reagent layer may be composed of plural different layers. Besides, the reagent layer may be an immunoassay reagent layer containing the component(s) reacting as an immunological reaction. A water-absorption layer may be interposed between the reagent layer or the registration layer and and support. In the above layer constitutions (1) to (3) and (6), a filtering layer may be interposed between the reagent layer and the spreading layer or the registration layer. In the above layer compositions (3) to (7), a filtering layer may be interposed between the light-reflecting layer and the spreading layer the reagent layer or the registration layer, between the reagent layer and the registration layer, or between the spreading layer and the reagent layer. When the reagent layer is composed of two or more layers, a filtering layer may be interposed between a reagent layer and another reagent layer. The reagent layer or the registration layer may be a porous reagent layer or a porous reigstration layer similar to the porous layer described later.

Preferred materials of the light-transmissive water-impermeable support are polyethylene terephthalate, polystyrene and the like.

In order to bind a hydrophilic layer securely, preferably, an undercoat layer is provided on the support, or the surface of the support is treated with a hydrophilic treatment. Whereas, the support may be a light-reflective or light-intransmissive (opaque) sheet, such as a white or milky white opaque polyethylene terephthalate film containing titanium dioxide particulates or barium sulfate particulates dispersed therein.

The water-permeable layer of the dry-type analytical element of the invention may be a substantially uniform layer containing a hydrophilic polymer or a porous layer disclosed, for example, in EP 0 166 365A, EP 0 226 465A, Japanese Patent KOKAI Nos. 701635/1983, 116258/1987, etc. The hydrophilic polymer may be selected from gelatin, gelatin derivatives such as phthalated gelatin, cellulose, agarose, polyacrylamide, polymethacrylamide, copolymers of acrylamide or methacrylamide and various vinyl monomers, and the like.

The material composing the porous layer may be filter paper, nonwoven fabric, woven fabric such as plain weave, knitted fabric such as tricot fabric, glass fiber filter paper or the like. As the spreading layer, woven fabrics and knitted fabrics are preferable among them. The woven fabrics and the like may be treated with glow discharge disclosed in GB 2 087 074A. A hydrophilic polymer or a surfactant may be incorporated in the spreading layer in order to controll the spreading area, the spreading speed and the like, as disclosed in EP 0 162 301A and DE 37 17 913A.

The immunoassay reagent layer is a water-permeable layer containing a part or all of the principal components of the immunoassay reagent composition in the analytical element of the invention which are:

(A) the water-insoluble macromolecular substrate (B) an antibody, reacting with the ligand in the sample, conjugated with an enzyme capable of acting on the above water-insoluble macromolecular substrate (C) the macromolecular substance which is a conjugate of the ligand or its derivative with a macromolecular compound.

When the analytical element of the invention contains the second antibody, this layer also contains a part or all of the second antibody. A suitable content of the macromolecular antigen is about 0.1 to 100 mg/m$^2$, preferably about 1 to 10 mg/m$^2$, a suitable content of the water-insoluble macromolecular substrate is about 1 mg/m$^2$ to about 20 g/m$^2$, preferably about 4 to 10 g/m$^2$, and a suitable content of the enzyme-antibody conjugate is about 0.1 to 100 mg/m$^2$, preferably about 1 to 10 mg/m$^2$. The immunoassay reagent layer may be composed of plural layers, and in this case, the above respective components may be separated into different layers.

More particularly, the dry-type analytical element of the invention may contain each of the enzyme-antibody conjugate (L1), the macromolecular antigen (L2) and the water-insoluble macromolecular substrate (S) in the following embodiments. The figure in the circle indicates an embodiment number.

| | ① | | | | | |
|---|---|---|---|---|---|---|
| Reagent Layer A | L1,S | | | | | |
| | ② | ③ | | | | |
| Reagent Layer A | L1, | S | | | | |
| Reagent Layer B | S | L1 | | | | |
| | ④ | | | | | |
| Reagent Layer A | L1,L2,S | | | | | |
| | ⑤ | ⑥ | ⑦ | ⑧ | ⑨ | ⑩ |
| Reagent Layer A | L1,L2 | L2,S | L1,S | S | L1 | L2 |
| Reagent Layer B | S | L1 | L2 | L1,L2 | L2,S | L1,S |
| | ⑪ | ⑫ | ⑬ | ⑭ | ⑮ | ⑯ |
| Reagent Layer A | S | S | L1 | L1 | L2 | L2 |
| Reagent Layer B | L1 | L2 | S | L2 | L1 | S |
| Reagent Layer C | L2 | L1 | L2 | S | S | L1 |

In every embodiment, a spreading layer may be provided on the opposite side of the reagent layer to the support, or the spreading layer may be combined with the reagent layer. Another reagent layer containing one or more reagents other than L1, L2 and S, such as a coloring reagent, may be incorporated in any of the above embodiments 1 to 16.

The reagent layer may contain a buffer such as a carbonate, a borate, a phosphate, Good's buffer described in Biochemistry, vol. 5, No. 2, pp 467–477 (1966) or the like. The buffer may be selected in the light of "Tanpakushitsu Koso no Kisojikken-Ho (Fundamental Experimentation Method of Proteins, Enzymes)" (Authers: Horio et al, Nankodo, 1981), the above Biochemistry reference, etc.

In the case of using the porous layer as the spreading layer, the porous layer preferably has a metering action being that a sample spotted on the spreading layer spreads at a fixed amount per unit area without uneven distribution of any component in the sample in lateral directions.

An adhesive layer may be provided on a reagent layer, a light-blocking layer or a light-reflecting layer, a filtering layer, a water-absorption layer, a registration layer or the like, in order to bind a porous layer. The adhesive layer is preferably composed of a hydrophilic polymer capable of adhering or integrating a porous layer, when the polymer is in swollen state, such as gelatin, gelatin derivatives, polyacrylamide or starch.

The light-blocking layer or a light-reflecting layer blocks the color of the sample spotted on a spreading layer, particularly the red color of hemoglobin in a whole blood sample, when the optically detectable change, such as, coloration or discoloration, occurring in a reagent layer, a registration layer or the like is measured by reflection photometry from the opposite side of the spreading layer. In addition, it also functions as a background layer. The light-reflecting layer is preferably a water-permeable layer composed of a hydrophilic polymer as a binder wherein light-reflecting particles, such as, titanium dioxide or barium sulfate are dispersed. Preferable hydrophilic polymers are gelatin, gelatin derivative, polyacrylamide, starch and the like.

The light-reflecting particles may also be incorporated into a spreading layer, a reagent layer, a registration layer or the like in addition to or instead of the light-reflecting layer.

The analytical element of the invention can be prepared according to a known method described in the foregoing patents.

The integral multilayer analytical element of the invention is preferably cut into square pieces having a side of about 15 mm to about 30 mm or circular pieces having a similar size or the like, and put in a slide frame disclosed in U.S. Pat. No. 4,169,751, Japanese Patent KOKAI No. 63452/1982, U.S. Pat. No. 4,387,990 and Japanese Utility Model KOKAI No. 32350/1983, U.S. Pat. No. 4,169,751, U.S. Pat. No. 4,387,990, International Publication WO 83/00391, etc. This analytical slide is preferable in view of production, packaging, transportation, stock, measuring operation and the like. While, the analytical element may be supplied in a form of a long tape packaged in a cassette or a magazine or in a form of small pieces stuck on or placed in a card having an opening.

The measurement is carried out, for example, according to the manner disclosed in the specifications of the foregoing patents. About 5 $\mu$l to about 30 $\mu$l, preferably about 8 $\mu$l to about 15 $\mu$l of an aqueous sample, such as whole blood, plasma, serum, lymph or urine, is spotted on the spreading layer, and incubated at a definite temperature in the range of about 20° C. to about 40° C., preferably at 37° C. or its vicinity for 1 to 10 minutes, preferably 2 to 7 minutes. Thereafter, the coloration or discoloration occurred in the analytical element is measured from the side of the support through reflection photometry using the visible or ultraviolet light having the wave length of a maximum absorption or its vicinity. The ligand content of the sample is determined by the principle of colorimetry using a previously prepared calibration curve. Instead, it is also possible that a fluorescence intensity emitted from the analytical element is measured, and the ligand content of the sample is determined by using a calibration curve prepared previously. A quantitative analysis of the ligand can be conducted in a high accuracy by fixing the spotted amount of a liquid sample, the incubation time and the temperature. In the embodiment of using a light-reflecting or opaque support, the coloration or discoloration occurred in the analytical element is measured from the side of the topmost layer being the opposite side of the support through reflection photometry.

When this measurement is carried out by using the chemical-analytical apparatus disclosed in U.S. Pat. No. 4,488,810, U.S. Pat. No. 4,424,191 and U.S. Pat. No. 4,424,191, highly accurate results can easily be obtained by a simple operation.

EXAMPLES

Example 1

(1) Preparation of Enzyme-Antibody Conjugate (i) Preparation of CHM-induced $\alpha$-amylase 5 mg of Bacillus subtilis α-amylase was dissolved in 1 ml of 0.1M glycerophosphate buffer solution of pH 6.3. 100 μl of 2 mg/ml 4-maleimidomethylcyclohexane-1-carboxylic acid N-hydroxysuccinimide ester (CHMS) dimethylformamide (DMF) solution was added to this α-amylase solution, and allowed to stand at room temperature for 1 hour. The reaction mixture was introduced into a Sephadex G-25 column, and gel filtration was carried out by using 0.1M glycerophosphate buffer solution of pH 6.3. The void fractions were collected to obtain the desired CHM-induced α-amylase.

(ii) Preparation of anti-theophylline mouse IgG F(ab')$_2$

300 μg of papain was added to 2 ml of 0.1M acetate buffer solution of pH 5.5 containing 10 mg of anti-theophylline mouse IgG, and stirred at 37° C. for 18 hours. This reaction solution adjusted to pH 6.0 by adding 0.1N NaOH was introduced in an AcA-44 gel column previously equilibrated with 0.1M phosphate-buffered 1 mM EDTA solution of pH 6.3, and eluted by the above phosphate buffer solution. The peak portion eluted around the molecular weight of 100,000 was collected and concentrated to 1 ml to obtain the object anti-theophylline mouse IgG F(ab')$_2$.

(iii) Preparation of α-amylase-anti-theophylline mouse IgG Fab' conjugate 1 ml of 0.1M phosphate-buffered 1 mM EDTA solution of pH 6.0 containing 6 mg of the above anti-theophylline mouse IgG F(ab')$_2$ was mixed with 100 μl of 10 mg/ml 2-mercaptoethylamine hydrochloride aqueous solution, and allowed to stand at 37° C. for 90 minutes. Gel filtration using a Sephadex G-25 column which was previously equilibrated with 0.1M glycerophosphate buffer solution of pH 6.0 was carried out, and unreacted 2-mercaptoethylamine was removed to obtain Fab'. 2 mg of CHM-induced α-amylase prepared in item i) was added, and allowed to react at 37° C. for 90 minutes. Subsequently, this reaction solution was separated by gel filtration using an AcA-34 column which was equilibrated with 0.1M acetate-buffered 5 mM calcium chloride solution of pH 7.0, and the fractions corresponding to the molecular weights of greater than 200,000 were collected. The fractions were concentrated to obtain the object conjugate.

(2) Synthesis of Macromolecular Antigen (Horse Ferritin-Theophylline Conjugate)

5 mg of 8-propylcarboxytheophylline dissolved in 100 μl of dimethylformamide (DMF) was mixed with 3 mg of N-hydroxysuccinimide and 5 mg of water-soluble carbodiimide, and stirred at room temperature for 2 hours to obtain activated theophylline solution. 500 μl of the above activated theophylline solution was added to 10 mg of horse ferritin dissolved in 1 ml of 0.1M sodium hydrogen carbonate aqueous solution, and allowed to stand at room themperature for 1 hour. Unreacted substances were removed by using a Sephadex G-25 gel column previously equilibrated with a phosphate-buffered saline solution of pH 7.0 to obtain 9 mg of the object macromolecular antigen of horse ferritin-theophylline conjugate.

(3) Preparation of Water-Insoluble Dye Starch 40 g of carboxymethylstarch ("Explotab", Kimura Sangyo Co., Ltd.) was suspended in 1500 ml of distilled water. 8 g of Diamira Brilliant Blue R (C.I. Number 61200, Mitsubishi Chimical Industries) was added to the suspension, and stirred at room temperature for 30 minutes. 150 g of sodium sulfate anhydrate was added to the suspension, and further stirred at room temperature for 30 minutes. Subsequently, 45 g of sodium carbonate was added, and stirred at 45° C. overnight. Then, the suspension was centrifuged, and precipitates were collected. The precipitates were suspended in distilled water, and then centrifuged to recover them. The above washing was repeated until the supernatant was not colored. Finally, the precipitates were washed with ethanol, and dried.

(4) Preparation of Dry-Type Analytical Element

Onto a colorless transparent polyethylene terephthalate (PET) sheet support 180 μm thick on which a gelatin undercoat layer was provided, the following aqueous solution was applied so as to become the following coating amount, and dried to form a crosslinking agent-containing water-absorption layer.

| | |
|---|---|
| Alkali-treated gelatin | 10 g/m$^2$ |
| Nonylphenoxypolyglycidol | 330 mg/m$^2$ |
| (Containing 10 glycidol units on average) | |
| Bis[(vinylsulfonylmethylcarbonyl)amino]methane | 400 mg/m$^2$ |

Onto the crosslinking agent-containing water-absorption layer, the following aqueous suspension was applied so as to become the following coating amount, and dried to form a registration layer.

| | |
|---|---|
| Acid-treated gelatin | 10 g/m$^2$ |
| Polymer aqueous latex (1)* | 3 g/m$^2$ |
| (Containing 10% of solid matter) | |
| Nonylphenoxypolyglycidol | 2 g/m$^2$ |
| (Containing 10 glycidol units on average) | |

*[(p-Divinylbenzene)$_x$-(styrene)$_y$-((1-piperidininmethyl) styrene chloride)$_w$]terpolymer x:y:w = 5:47.5:47.5

Onto the registration layer, the following aqueous suspension was applied so as to become the following coating amount, and dried to form a light-blocking layer having a dry thickness of 7 μm.

| | |
|---|---|
| Alkali-treated gelatin | 2.9 g/m$^2$ |
| Ratile type titanium dioxide particulates | 13 g/m$^2$ |
| Nonylphenoxypolyglycidol | 400 mg/m$^2$ |
| (Containing 10 glycidol units on average) | |

Onto the light-blocking layer, the following aqueous solution was applied so as to become the following coating amount, and dried to form a binding layer having a dry thickness of 5 μm.

| | |
|---|---|
| Alkali-treated gelatin | 6.7 g/m$^2$ |
| Nonylphenoxypolyglycidol | 600 mg/m$^2$ |
| (Containing 10 glycidol units on average) | |

The surface of the binding layer was uniformly moistened with 30 g/m$^2$ of water, and a cellulose acetate membrane filter about 140 μm thick having a nominal pore size of 3.0 μm was laminated thereon as the porous registration layer.

Subsequently, the following composition was applied onto the porous registration layer, and dried.

| | |
|---|---|
| Amylase-anti-theophylline mouse IgG Fab' | 4.0 mg/m$^2$ |
| Nonylphenoxypolyethyoxyethanol | 200 mg/m$^2$ |

A tricot fabric about 250 μm thick made by knitting 50 deniers PET span yarn using 36 gauge containing the following reagent composition was provided as the porous spreading layer by laminating it onto the porous registration layer.

| | |
|---|---|
| Dye-labeled starch | 7 g/m² |
| Horse ferritin-theophylline | 4.2 mg/m² |
| Nonylphenoxypolyethoxyethanol | 500 mg/m² |

The integral multilayer analytical element for immunoassay thus prepared was cut into square tips having a side of 15 mm, and each tip was placed in a slide frame disclosed in Japanese Patent KOKAI No. 63452/1982 to complete a multilayer analytical slide (1) for the analysis of theophylline.

(5) Evaluation Test

20 μl of 50 mM glycerophosphate buffer solution of pH 7 containing a known amount of theophylline was spotted onto the spreading layer of the above multilayer analytical slide (1) for the analysis of theophylline. After incubating at 37° C. for 20 minutes, the reflection optical density at 640 nm was measured from the side of the support. The results are shown in FIG. 1.

By the calibration curve of FIG. 1, it was found that the content of theophylline can be determined by the dry-type analytical element for immunoassay for the analysis of theophilline accurately.

Example 2

(1) Preparation of Enzyme-Antibody Conjugate (i) Preparation of anti-human ferritin goat IgG F(ab')₂

0.5 mg of pepsin was added to 2 ml of 0.1M acetate buffer solution of pH 4.2 containing 10 mg of anti-human ferritin goat IgG, and stirred at 37° C. overnight. This reaction solution adjusted to pH 7.0 by adding 0.1N NaOH was introduced in an AcA-44 gel column previously equilibrated with 0.1M phosphate-buffered 1 mM EDTA solution of pH 6.0, and eluted by the above phosphate buffer solution. The peak portion eluted around the molecular weight of 100,000 was collected and concentrated to 1 ml to obtain the object anti-human ferritin goat IgG F(ab')₂.

(ii) Preparation of α-amylase-anti-human ferritin goat IgG Fab' conjugate 1 ml of 0.1M phosphate buffered 1 mM EDTA solution of pH 6.0 containing 6 mg of the above anti-human ferritin goat IgG F(ab')₂ was mixed with 100 μl of 0.1M 2-mercaptoethylamine hydrochloride aqueous solution, and incubated at 37° C. for 2 hours. Gel filtration using a Sephadex G-25 column which was previously equilibrated with 0.1M glycerophosphate buffer solution of pH 7.0 was carried out, and unreacted 2-mercaptoethylamine was removed to obtain 5 mg of Fab'. 0.62 mg of CHM-induced α-amylase prepared in Example 1 (1) i) was added to the Fab' solution, and allowed to stand at 4° C. overnight. Subsequently, this reaction solution was concentrated to 1 ml with PEG 20,000, and then, separated by gel filtration using a Sephacryl S-300 column which was equilibrated with 0.1M glycerophosphate-buffered 5 mM calcium chloride solution of pH 7.0. The protein fractions corresponding to the molecular weights of about 200,000 to 300,000 daltons were collected to obtain the object conjugate.

(2) Preparation of Dry-Type Analytical Element

A crosslinking agent-containing water-absorption layer was provided on a PET support in the same manner as Example 1.

Onto the crosslinking agent-containing water-absorption layer, the following aqueous solution was applied so as to become the following coating amount, and dried to form a binding layer having a dry thickness of 5 μm.

| | |
|---|---|
| Alkali-treated gelatin | 6.7 g/m² |
| Nonylphenoxypolyglycidol | 600 mg/m² |
| (Containing 10 glycidol units on average) | |

The surface of the binding layer was uniformly moistened with 30 g/m² of water, and a cellulose acetate membrane filter about 140 μm thick having a nominal pore size of 3.0 μm was laminated thereon as the porous registration layer.

A tricot fabric about 250 μm thick made by knitting 50 deniers PET span yarn using 36 gauge containing the following reagent composition was provided as the porous spreading layer by laminating it onto the porous registration layer.

| | |
|---|---|
| Dye-labeled starch | 7.2 g/m² |
| α-Amylase-anti-human ferritin goat IgG Fab' | 2 mg/m² |
| Nonylphenoxypolyethoxyethanol | 500 mg/m² |
| (Containing 10 hydroxyethylene units on average) | |

The integral multilayer analytical element for immunoassay thus prepared was cut into square tips having a side of 15 mm, and each tip was placed in a slide frame disclosed in Japanese Patent KOKAI No. 63452/1982 to complete a multilayer analytical slide (2) for the analysis of ferritin.

(3) Evaluation Test

20 μl of 50 mM glycerophosphate buffer solution of pH 7.0 containing a known amount of ferritin was spotted onto the spreading layer of the above multilayer analytical slide (2) for the analysis of ferritin. After incubating at 37° C. for 30 minutes, the reflection optical density at 640 nm was measured from the side of the support. The results are shown in FIG. 2.

Figure 2:
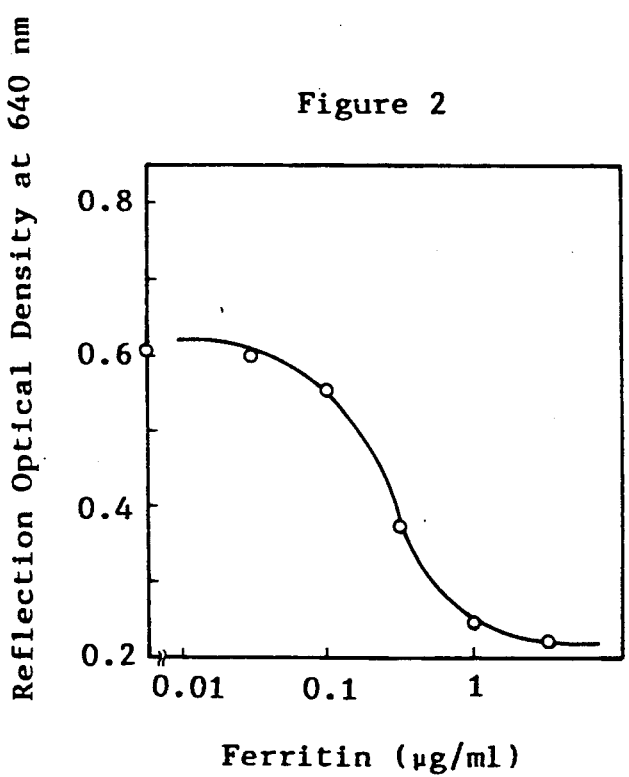
FIG. 2 indicates a calibration curve of ferritin using the dry-type analytical element for immunoassay obtained in Example 2.

By the calibration curve of FIG. 2, it was found that the content of ferritin can be determined by the dry-type analytical element for immunoassay for the analysis of ferritin accurately.

We claim:

1. In a dry multilayer analytical element for measuring a ligand in a liquid sample by enzyme immunoassay, wherein one of said layers is a reagent layer, the improvement which comprises said reagent layer containing at least one porous layer, said porous layer comprising:

(a) a water-insoluble macromolecular substrate; and
(b) an antibody which is reactive with the ligand in the sample and is conjugated with an enzyme, said enzyme being capable of digesting the water-insoluble macromolecular substrate and the activity of the enzyme/antibody in the conjugate being effected relative to the steric hindrance effect when the ligand is bound to the enzyme/antibody conjugate.

2. In a dry multi-layer analytical element for measuring a ligand in a liquid sample by enzyme immunoassay, wherein one of said layers is a reagent layer, the improvement which comprises said reagent layer containing at least one porous layer, said porous layer comprising:

(a) a water-insoluble macromolecular substrate; and
(b) an antibody which is reactive with the ligand in the sample and is conjugated with an enzyme, said enzyme being capable of digesting the water-insoluble macromolecular substrate and the activity of the enzyme/antibody in the conjugate being effected relative to the steric hindrance effect when the ligand is bound to the enzyme/antibody conjugate; and
(c) a conjugate of the ligand with a macromolecular compound.

3. The analytical element of claim 1 having at least two water-permeable layers and at least one of the water-permeable layers being a porous layer.

4. The analytical element of claim 1 which further comprises another antibody specific to different antigenic determinant from that to the antibody conjugated with the enzyme.

5. The analytical element of claim 2 having at least two water-permeable layers and at least one of the water-permeable layers being a porous layer.

6. The analytical element of claim 2 which further comprises another antibody specific to a different antigenic determinant from that to the antibody conjugated with the enzyme.

7. The analytical element of claim 1 wherein a directly or indirectly detectable functional group or compound is bound to said water-insoluble macromolecular substrate.

8. The analytical element of claim 2 wherein a directly or indirectly detectable functional group or compound is bound to said water-insoluble macromolecular substrate.

9. The analytical element of claim 7 wherein said directly or indirectly detectable functional group or compound is a compound having a dye portion or capable of producing fluorescence of luminescence.

10. The analytical element of claim 8 wherein said directly or indirectly detectable functional group or compound is a compound having a dye portion or capable of producing fluorescence of luminescence.

* * * * *